United States Patent
Fudge et al.

(10) Patent No.: US 6,941,162 B2
(45) Date of Patent: Sep. 6, 2005

(54) PULSE OXIMETRY SENSOR AND DISPENSING METHOD

(75) Inventors: Brian M. Fudge, Middletown, CT (US); Kimberley A. Golden, Wallingford, CT (US); David R. Rich, Glastonbury, CT (US)

(73) Assignee: Respironics Novametrix, Inc., Wallingford, CT (US)

( * ) Notice: Subject to any disclaimer, the term of this patent is extended or adjusted under 35 U.S.C. 154(b) by 0 days.

(21) Appl. No.: 10/748,074

(22) Filed: Dec. 29, 2003

(65) Prior Publication Data

US 2004/0143172 A1 Jul. 22, 2004

Related U.S. Application Data

(63) Continuation of application No. 10/242,866, filed on Sep. 13, 2002, now Pat. No. 6,671,532.
(60) Provisional application No. 60/322,724, filed on Sep. 17, 2001.

(51) Int. Cl.[7] .......................... A61B 5/00; B65D 85/66
(52) U.S. Cl. .......................................... 600/344; 221/26
(58) Field of Search ............................... 600/310, 323, 600/340, 344; 221/26, 30, 32, 33; 206/278, 438; 224/673.2

(56) References Cited

U.S. PATENT DOCUMENTS

| | | | |
|---|---|---|---|
| 4,640,289 A | * | 2/1987 | Craighead .................. 600/391 |
| 4,685,464 A | | 8/1987 | Goldberger et al. |
| 4,773,532 A | | 9/1988 | Stephenson |
| 4,825,879 A | | 5/1989 | Tan et al. |
| 4,830,014 A | | 5/1989 | Goodman et al. |
| 4,865,038 A | | 9/1989 | Rich et al. |
| 5,170,786 A | | 12/1992 | Thomas et al. |
| 5,209,230 A | | 5/1993 | Swedlow et al. |
| 5,217,012 A | | 6/1993 | Young et al. |
| 5,337,744 A | | 8/1994 | Branigan |
| 5,437,275 A | | 8/1995 | Amundsen et al. |
| 5,438,986 A | | 8/1995 | Disch et al. |
| 5,465,714 A | | 11/1995 | Scheuing |
| 5,469,845 A | | 11/1995 | DeLonzor et al. |
| 5,999,834 A | | 12/1999 | Wang et al. |
| 6,256,523 B1 | | 7/2001 | Diab et al. |
| 6,671,532 B1 | * | 12/2003 | Fudge et al. ................ 600/344 |

* cited by examiner

*Primary Examiner*—Eric F. Winakur
(74) *Attorney, Agent, or Firm*—Michael W. Haas

(57) ABSTRACT

An oximetry sensor that can be easily applied and attached to a portion of the body of a patient in a noninvasive manner is provided. The oximetry sensor of the present invention includes an adhesive wrap member for use with reusable pulse oximetry sensor electronics (e.g., an LED assembly and a photodiode coupled with a cable) to retain the sensor in the desired position comfortably on a patient. The adhesive member includes a release liner thereover which may include an appliqué or other member thereon, for example, instructions for use. The release liner is configured for removal from the adhesive member in at least one release liner portion subsequent to attaching of the pulse oximetry sensor electronics without disturbing such positioning.

15 Claims, 9 Drawing Sheets

PULSE OXIMETRY SENSOR AND DISPENSING METHOD

CROSS REFERENCE TO RELATED APPLICATIONS

Under the provisions of 35 U.S.C. § 119(e), this application claims the benefit of U.S. Provisional Application Ser. No. 60/322,724, filed Sep. 17, 2001, which is hereby incorporated by this reference as if set forth in its entirety herein.

BACKGROUND OF THE INVENTION

1. Field of the Invention

The present invention is related to sensors applied to the body of a patient for monitoring or making measurements of body tissue conditions, metabolism, or other body functions indicative of health. More specifically, the present invention is directed to a pulse oximetry sensor that can be easily applied and attached to a portion of the body of a patient in a noninvasive manner having an adhesive wrap member for use with reusable pulse oximetry sensor electronics to retain the sensor in the desired position comfortably on a patient.

2. Description of the Related Art

It is known to use a noninvasive pulse oximetry sensor to measure the relative oxygen saturation of the blood. Typically, in such oximetry sensors, a light source, such as a light emitting diode (LED), is used to alternately direct light of two different wavelengths, such as red light and infrared light, to the blood through the skin. The light transmitted or reflected by the blood at the different wavelengths can then be compared to provide a measurement of oxygen saturation of the blood.

A typical oximetry probe system contains light emitting sources, such as LEDs, and a light detector, such as a photodiode, mounted on an appendage of the body, such as a finger, toe, ear lobe, nose, hand, tongue, or foot. However, such devices need to be capable of being easily and readily attached to the body appendages, comfortable when attached to the patient, and reusable on the same patient. Additionally, such devices must be relatively inexpensive to manufacture, remain in the desired position on the patient during use without substantial movement, and fit a wide variety of patients without discomfort.

Conventional oximetry sensors use various methods to apply and retain the sensor on a patient. Such methods include, for example, mechanical clamping, deformable members, hooks and loops, adhesives and elastomeric members.

One type of oximetry sensor uses the mechanical clamping action of spring biased jaws to retain the sensor on an appendage of a patient. Such a device is illustrated in U.S. Pat. No. 4,685,464, issued to Goldberger et al. on Aug. 11, 1987, and U.S. Pat. No. 5,438,986, issued to Disch et al. on Aug. 8, 1995. While such devices are effective, they are inherently difficult to clean and inappropriate for long term use or application on a patient. Furthermore, such devices may only be used on the fingers of a patient. The clamping pressure of the spring biased jaws necessary to maintain the oximetry sensor in position on the patient's finger often is uncomfortable during long-term usage.

Another type of oximetry sensor relies upon a deformable member being located in the device to retain the sensor on an appendage of a patient. Such a device is illustrated in U.S. Pat. No. 4,865,038, issued to Rich et al. on Sep. 12, 1989 and U.S. Pat. No. 5,217,012, issued to Young et al. on Jun. 8, 1993. Because the retaining member of these types of sensors is deformed upon first use and has a memory, reinstallation of the sensor may affect the comfort of the patient during reuse.

Yet another type of pulse oximetry sensor comprises a photoemitter, a photodetector and a generally tubular housing having an inner wall, an outer wall and a lumen for receiving a body part of a patient. The housing further includes a pair of opposed pockets for removably receiving the photoemitter and the photodetector. Such a sensor is illustrated in U.S. Pat. No. 5,437,275, issued to Amundsen et al. on Aug. 1, 1995. The wrap member forming the housing comprises a wrap of a disposable material, such as paper, which may be preassembled or custom formed into the desired shape. However, such a wrap member may be used only once without deterioration thereof.

For another type of pulse oximetry sensor, a disposable optical probe includes a central portion, a pair of adhesive flanges extending from the central portion, a connector portion situated between the flanges and a pair of small adhesive flaps extending from the central portion on the end of the optical probe opposite the connector. The probe further includes a connection aperture formed in the connector portion and an emitter aperture with an emitter (e.g., a light-emitting diode) positioned within the central portion close to the connector portion. A flex pocket is located within the central portion between the emitter aperture and a detector aperture which allows light to pass through the detector aperture to a detector assembly. The probe is fabricated from multiple layers, including a flex circuit layer, a Mylar™ layer, a face stock tape layer and other tape layers. Typically, the disposable optical probe is wrapped around the end of a patient's finger during use and is secured in position by adhesive on the flaps. However, reuse of the optical probe is not typically successful because the adhesive deteriorates with each use allowing the optical probe to move.

In another instance, in an effort to facilitate reuse of a pulse oximetry sensor and to provide comfort to the patient, the sensor is retained on the finger of a patient through the use of hook and loop fabric. However, such sensors typically have used complex shapes of hook and loop fabric to retain the device thereby causing the manufacturing expense of the device to increase. Also, the sensors may need to be installed tightly on an appendage to prevent movement thereby causing discomfort for the patient. Such sensors are illustrated in U.S. Pat. No. 4,825,879, issued to Tan et al. on May 2, 1989, U. S. Pat. No. 5,209,230, issued to Swedlow et al. on May 11, 1993 and U.S. Pat. No. 5,469,845, issued to DeLonzor et al. on Nov. 28, 1995.

In another type of oximetry sensor having an adhesive, the adhesive is used to attach the sensor to an appendage of a patient in an attempt to lower manufacturing cost of the sensor, provide comfort to the patient during use of the sensor and provide a secure attachment of the sensor to the patient. However, because the sensor must often be repositioned on a patient, the adhesive loses its adhesive quality during reuse thereby allowing movement of the sensor. Also, the adhesive may irritate the patient during use, thereby causing discomfort. Such sensors are illustrated in U.S. Pat. No. 4,830,014, issued to Goodman et al. on May 16, 1989 and U.S. Pat. No. 5,170,786, issued to Thomas et al. on Dec. 15, 1992.

Again, in yet another type of oximetry sensor, an elastomeric member is used to retain the sensor on the finger of a patient. Although this allows the reuse of the sensor, the degree of pressure applied by the elastomeric member and the elastomeric member being in contact with the skin, may cause discomfort to a patient and, if too weak, may allow movement of the sensor during use. Such a sensor is illustrated in U.S. Pat. No. 5,337,744, issued to Branigan on Aug. 16, 1994.

In U.S. Pat. No. 5,999,834, entitled "Disposable adhesive wrap for use with reusable pulse oximetry sensor and method of making" ("the '834 patent"), issued to Wang on Dec. 7, 1999, a design is presented that overcomes many of the shortcomings of the conventional devices. Illustrated and described is a pulse oximetry sensor having a wrap member including a fastener, an adhesive member initially having a removable cover thereover, a release liner located thereover, an LED assembly, and a photodiode. The LED assembly and photodiode of the '834 patent are connected to a cable. In use, this sensor also may be subject to the adhesive quality being degraded by the repositioning of the sensor on an appendage of a patient or the movement of the sensor to another appendage.

Further illustrated in U.S. Pat. No. 6,256,523, issued to Diab et al. on Jul. 3, 2001 and U.S. Pat. No. 5,437,275, issued to Amundsen et al. on Aug. 1, 1995, are still other sensors having a wrap formed of multiple layers for use on an appendage of a patient.

The wraps used with the pulse oximetry sensors as discussed herein are typically located in a storeroom for respiratory equipment supplies or may be strewn about a patient's room or elsewhere. For convenience, wraps for oximetry sensors are typically packaged in bulk in a box in quantities of 100 wraps per box and, as such, are not conducive for ease of use at the point of care since a box of wraps would need to be kept in many locations of a care facility.

As discussed above, the conventional wraps or oximetry sensors are generally either reusable or expensive to manufacture, or are not easily reusable and have a relatively low manufacturing cost. Prior art wraps also may be reusable and cause discomfort to the patient. Accordingly, a pulse oximetry sensor that can be readily positioned on a patient and that is comfortable during use by a patient would be advantageous. Further, it would be desirable to manufacture a wrap that has an extended life, is reusable, has a disposable wrap member and has a low manufacturing cost.

SUMMARY OF THE INVENTION

Accordingly, it is an object of the present invention to provide an oximetry sensor that overcomes the shortcomings of conventional sensors. This object is achieved according to one embodiment of the present invention by providing an oximetry sensor that includes a disposable wrap member portion of a readily positioned, comfortable, extended life, reusable pulse oximetry sensor. The wrap member includes a plurality of apertures therein, and an adhesive member surrounding the plurality of apertures, the wrap member has a butterfly shape, an elongated strip shape or a shape for providing a fastener on at least one end thereof. An LED assembly is secured in a first of the plurality of apertures in the wrap member, and a photodiode is secured in a second of the plurality of apertures in the wrap member.

It is yet another object of the present invention to provide a method of making an oximetry sensor that does not suffer from the disadvantages associated with conventional manufacturing techniques. This object is achieved by providing a method that includes: 1) providing an LED assembly having a housing including two flanges; 2) providing a photodiode having a housing including two flanges; and 3) providing a wrap member having a cloth cover. The wrap member includes a fastener that is either an adhesive fastener and/or a hook and loop fastener. The wrap member also includes an adhesive member secured to the wrap member and having a removable liner thereover. The removable liner includes at least one of an appliqué removably coupled with the wrap member and another member coupled with the wrap member. Finally, the wrap member include a plurality of apertures therethrough. The method of the present invention further includes: 4) inserting the photodiode within a first of the plurality of apertures in the wrap member; and 5) inserting the LED assembly within a second of the plurality of apertures in the wrap member.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
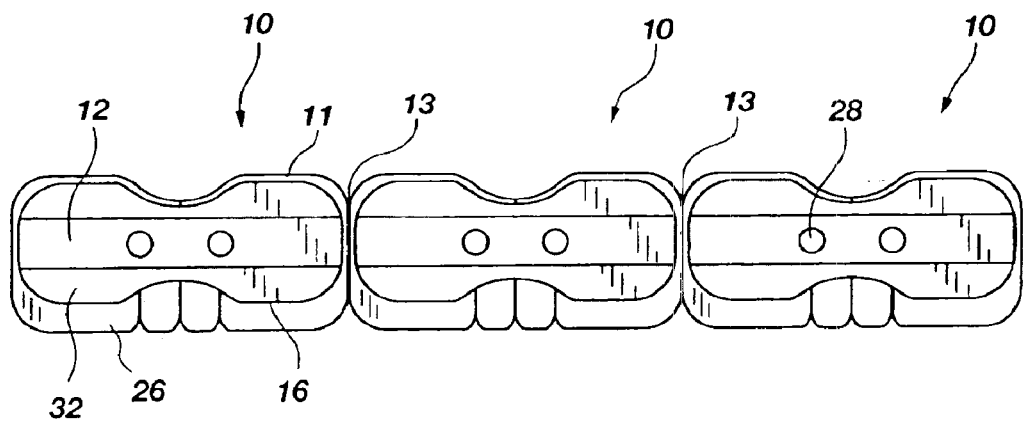
FIG. 1 is a front view of one embodiment of a disposable butterfly wrap member of the present invention depicted in strip form with other wrap members.

The present invention is directed to pulse oximetry sensors that can be easily applied and attached to a portion of the body of a patient in a noninvasive manner. The sensors have an adhesive wrap member for use with reusable pulse oximetry sensor electronics to retain the sensor in the desired position comfortably on a patient. The particular embodiments described herein are intended in all respects to be illustrative rather than restrictive. Alternative embodiments will become apparent to those of ordinary skill in the art to which the present invention pertains without departing from its scope.

Referring to the drawing figures in general, and initially to FIGS. 1–2B and 8–10 in particular, a disposable butterfly wrap member 10 of the present invention is shown in strip form having other butterfly wrap members 10 connected thereto and separated therefrom by perforations 13 located between the individual butterfly wrap members 10. Perforations 13 located between the individual butterfly wrap members 10 may be of any size or shape sufficient to allow each individual butterfly wrap member 10 to be readily separated from an adjacent butterfly wrap member 10 by hand.

Figure 11:
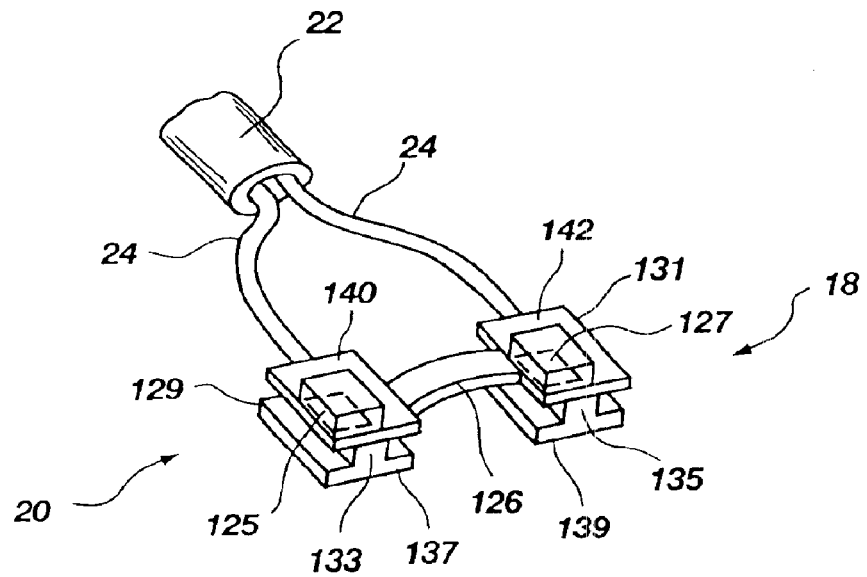
FIG. 11 is an enlarged view of the LED assembly, photodiode and portion of the connecting cable of the present invention.
Figure 12:
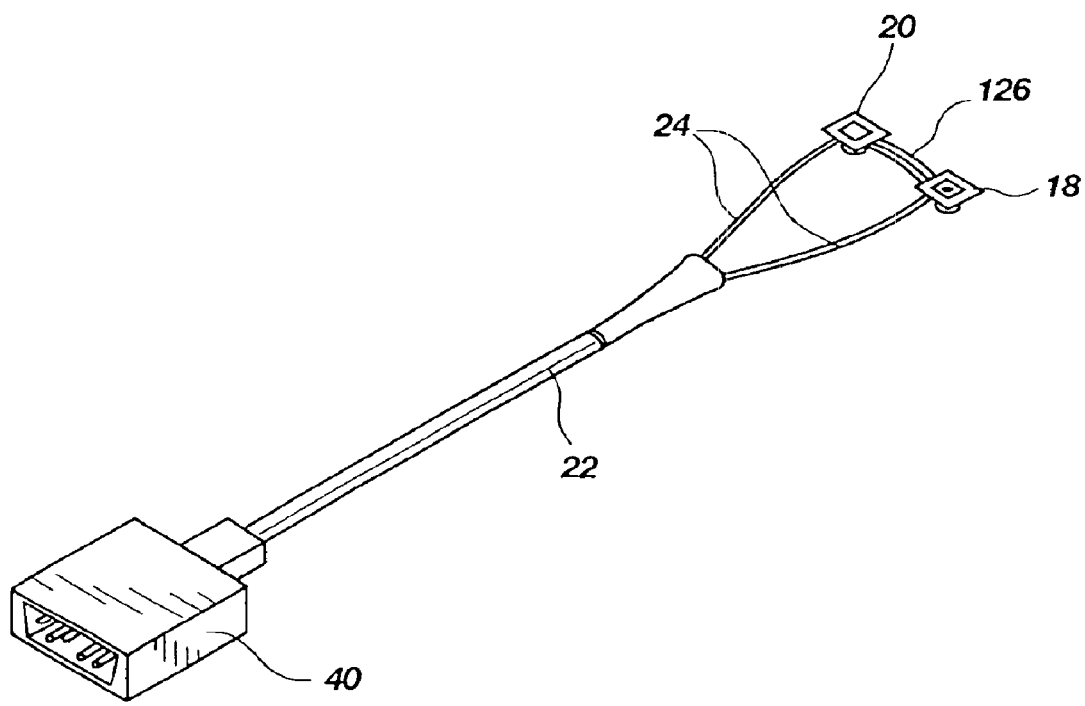
FIG. 12 is a view of the combination of an embodiment of a disposable wrap member, LED assembly, photodiode, cable, and connector of the present invention.
Figure 13:
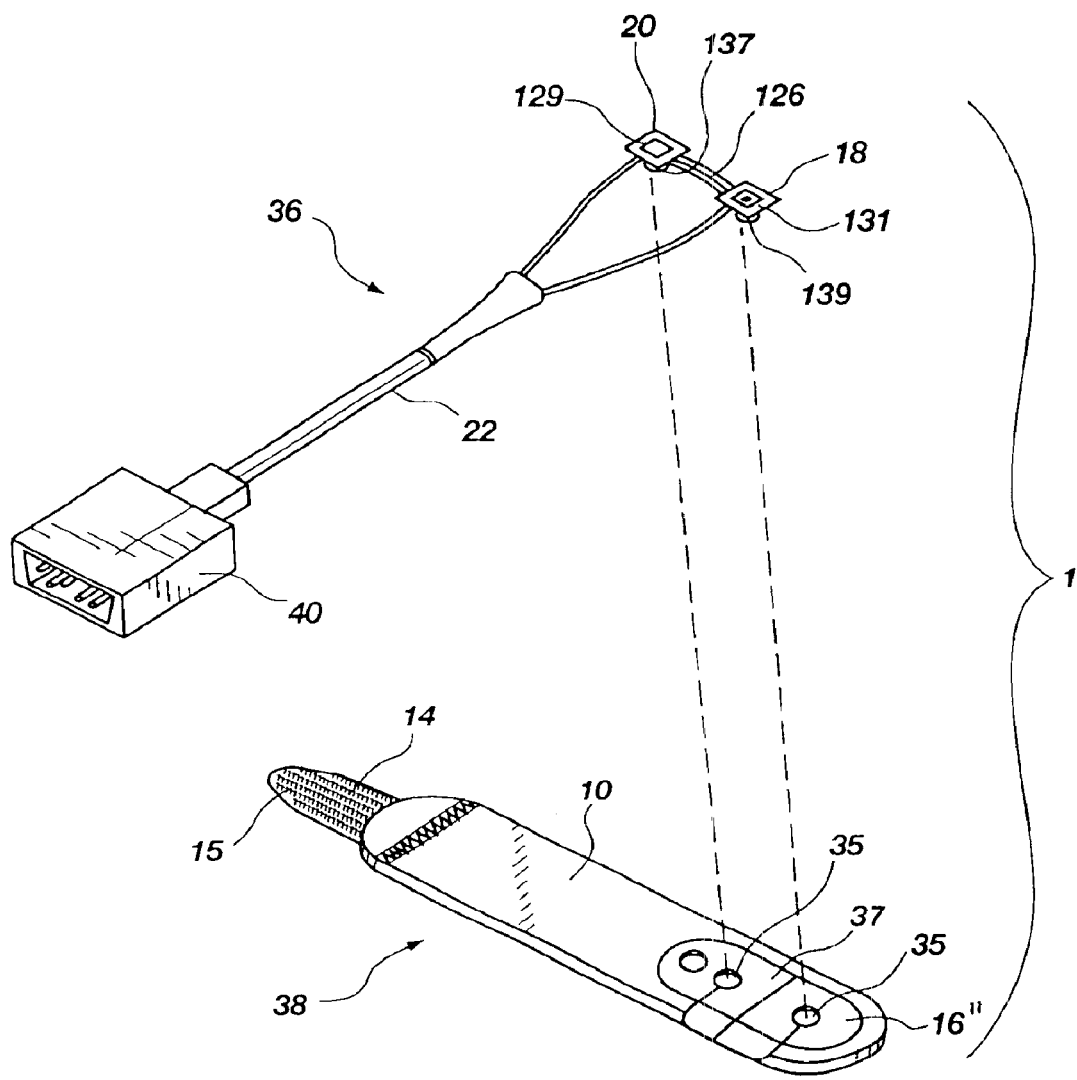
FIG. 13 is a view of a disposable wrap member of the present invention illustrating the insertion of the LED assembly and photodiode into the wrap member.

Butterfly wrap member 10 comprises a fabric cover 32 having a plurality of apertures 28 for portions of an LED assembly 18 (see FIGS. 11–13) and photodiode 20 therein (see FIGS. 11–13). If desired, fabric cover 32 may include a foam portion for the butterfly wrap member 10 comprising any suitable type foam, such as a polyester foam, or any suitable compliant substrate, foam substrate, comfortable foam substrate, or plastic foam substrate as the foam member. Fabric portion 32 of butterfly wrap member 10 comprises any suitable fabric, which may be readily engaged by the adhesive on the opposing side of the wrap member 10, as more fully described below. If included in the wrap member 10, the foam portion may be secured together by any suitable means of fastening, such as adhesive bonding.

Located on the opposing side of the butterfly wrap member 10 is an adhesive member 16 over or covering at least portions, or the entire surface of fabric portion 32 of butterfly wrap member 10. Adhesive member 16 located on fabric portion 32 may be any suitable type, such as a double-sided adhesive tape coated with a suitable adhesive, one side of adhesive member 16 being adhesively secured to wrap member 10, while the other side thereof initially has a suitable material covering 26, i.e., a release liner, releasably retained thereover that is removed for installation of butterfly wrap member 10 of an oximetry sensor 1 (see FIG. 13) of the present invention on a patient.

Adhesive member 16 may have the shape of butterfly wrap member 10 to completely cover one side thereof or may be any convenient shape, such as a generally rectangular shaped member secured to wrap member 10. If desired, adhesive member 16 may be of any other suitable shape, such as an annular member. Adhesive member 16 is used to retain the oximetry sensor of the present invention in position on a patient.

Figure 2A:
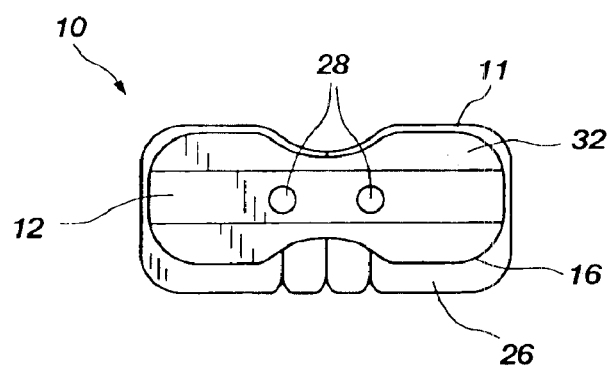
FIG. 2A is a front view of the embodiment of the disposable butterfly wrap member of the present invention depicted in FIG. 1.

Referring to FIG. 2A, an individual disposable butterfly wrap member 10 is illustrated having an optional cover strip 12 over a portion of a first side, e.g., the front side 11, of butterfly wrap member 10 and a plurality of apertures 28 for an LED assembly and photodiode. As further illustrated, portions of a release liner 26 are attached to portions of the opposing side, e.g., the back side (not shown), of butterfly wrap member 10. The release liner is illustrated in more detail in FIG. 2B.

Figure 2B:
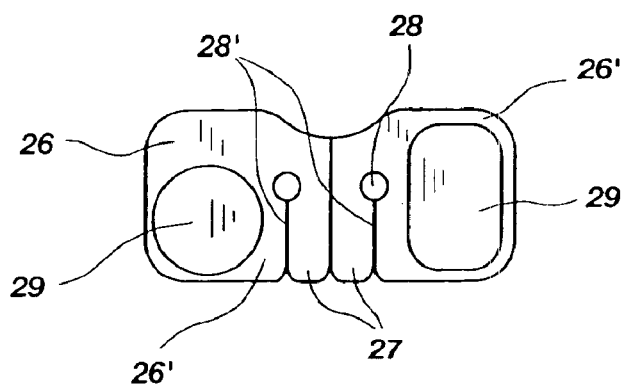
FIG. 2B is a rear view of the embodiment of the disposable butterfly wrap member of the present invention depicted in FIG. 1.

Referring to FIG. 2B, release liner 26 features a two-part wrap-around design including release liner portions 26' that each allows an LED assembly 18 (see FIG. 13) and photodiode 20 (see FIG. 13) to be assembled with butterfly wrap member 10 prior to the removal of release liner 26. This feature facilitates the assembly process and sharply reduces the chances that a user or member of a clinical staff will get stuck or tangled with the adhesive of adhesive member 16, on which release liner 26 is removably retained, during assembly of LED assembly 18 (see FIG. 13) and photodiode 20 (see FIG. 13) to butterfly wrap member 10.

Release liner 26 consists of two parts 26' each part having a release tab 27 for use by members of a clinical staff to pull or release release liner 26 from fabric cover 32 prior to applying the wrap member to the patient. Additionally, slits 28' are provided in release liner 26 to allow each part 26' of liner 26 to be peeled around the assembled LED assembly 18 (not shown) and photodiode 20 (not shown), each located in an aperture 28 in the butterfly wrap member 10.

Additionally, as illustrated, release liner 26 contains an appliqué 29 adhesively attached to a portion of the release liner 26 and another member 29' having, for example, instructions thereon, which may be adhesively attached to a portion of release liner 26 or be printed thereon. Any suitable adhesive may be used to attach appliqué 29 or instructions 29' to release liner 26, which is also suitable for use with the appliqué 29 on a patient or portion(s) of a patient's clothing. Appliqué 29 or 29'may have any type of shape or image thereon for use with the intended patient.

While the variety of shapes and types of disposable wrap member 10 is large, release liner 26 is most readily integrated into three variations of wrap members 10, each having a small and large size for use with patients of different physical size, such as neonatal, pediatric, and adult. The three variations of shapes for wrap members of the present invention can be generally described as, a butterfly wrap member (described above with respect to FIGS. 1–2B and 8–10), elongated strip wrap member (FIGS. 3–4B), and foam wrap member (FIGS. 5–7), which may be used to allow the pulse oximetry sensor of the present invention to be applied to patients ranging from neonates to adults. Additionally, the variations in the shape of the wrap members allows, particularly in neonates, the application of pulse oximetry sensor 1 (see, FIG. 13) to diverse sites including the hand, foot and finger. Butterfly wrap member 10 is preferably used on neonatal patients or pediatric patients on a variety of diverse sites.

Figure 3:
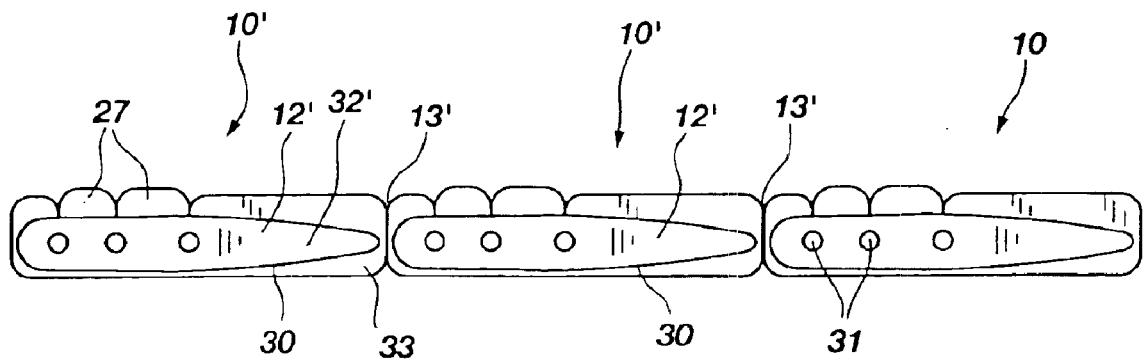
FIG. 3 is a front view of another embodiment of a disposable wrap member of the present invention depicted in strip form with other wrap members.
Figure 4A:
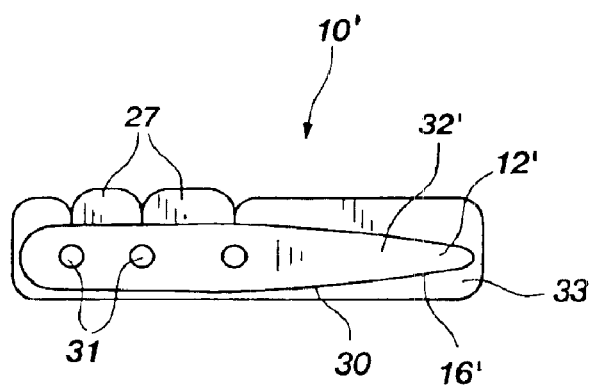
FIG. 4A is a front view of the embodiment of the disposable wrap member of the present invention depicted in FIG. 3.
Figure 4B:
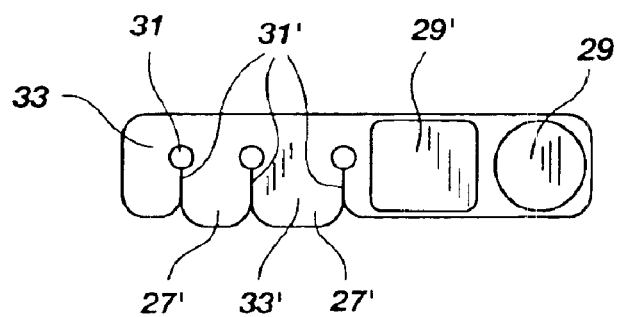
FIG. 4B is a rear view of the embodiment of the disposable wrap member of the present invention depicted in FIG. 3.

Referring to FIGS. 3–4B, another embodiment of the present invention is illustrated as an elongated strip wrap member 10' shown in strip form having other elongated strip wrap members 10' connected thereto and separated therefrom by perforations 13' located between the individual elongated strip wrap members 10'. Perforations 13' located between individual elongated strip wrap members 10' can be of any size or shape sufficient to allow each individual strip wrap member 10 to be readily separated from an adjacent strip wrap member 10'.

Elongated strip wrap member 10' comprises a fabric cover and a plurality of apertures 31 for portions of an LED assembly 18 (not shown) and photodiode 20 (not shown Fabric portion 32' of the elongated strip wrap member 10' comprises any suitable fabric, which may be readily engaged by the adhesive on the other side of wrap member 10' Located on the other side of elongated strip wrap member 10' is an adhesive member 16' over or covering at least portions of fabric portion 32 of elongate strip wrap member 10'.

Adhesive member 16' located on elongated strip wrap member 10' may be any suitable type, such as a double-sided adhesive tape coated with a suitable adhesive, one side of adhesive member 16' being adhesively secured to elongate strip wrap member 10', while the other side thereof initially has a suitable material covering 33, i.e., a release liner, releasably retained thereover that is removed for installation of the oximetry sensor of the present invention on a patient.

Adhesive member 16' may have the shape of elongated strip wrap member 10' to completely cover one side thereof or may be any convenient shape, such as a generally rectangular shaped member secured to elongated strip wrap member 10'. If desired, adhesive member 16' may be of any other suitable shape, such as an annular member. Adhesive member 16' is used to retain elongated strip wrap member 10' of the oximetry sensor 1 (see, FIG. 13) of the present invention in position on a patient.

Referring to FIG. 4A, an individual elongated strip wrap member 10' is illustrated having a cover strip 12' over a portion of one side, or the front side, of elongate strip wrap member 10' and apertures 31 for an LED assembly 18 (not shown) and photodiode 20 (not shown). As further illustrated, portions of a release liner 33 attached to portions of the opposing side, e.g., the back side (not shown), of the elongated strip wrap member 10.

Referring to FIG. 4B, the release liner 33 features a two-part wrap-around design including release liner portions 33' having tabs 27' thereon that allow an LED assembly 18 (not shown) and photodiode 20 (not shown) therein to be assembled with elongated strip wrap member 10' prior to the removal of portions 33' of release liner 33.

This feature facilitates the assembly process and sharply reduces the chances that a member of a clinical staff will get stuck or tangled with the adhesive located on adhesive member 16', on which release liner 33 is removably retained, during assembly of the LED assembly 18 (not shown) and photodiode 20 (not shown) therein to elongated strip wrap member 10'.

Release liner 33 consists of two parts 33' each having a release tab 27' for use by members of a clinical staff or any other user to pull to the release liner off of the fabric portion 30 and fabric portion 32' prior to applying the elongate strip wrap member to the patient. Additionally, there are slits 31' in liner 33 that allow each part 33' of liner 33 to be peeled around the assembled LED assembly 18 (not shown) and photodiode 20 (not shown) therein. Additionally, as illustrated, release liner 33 contains an appliqué or sticker 29 adhesively attached to a portion of the release liner 33 and another member 29', having, for example, instructions thereon, which may be adhesively attached to a portion of the release liner 33 or printed thereon. Any suitable adhesive may be used to attach appliqué 29 or instructions 29' to release liner 33, which is also suitable for use with appliqué 29 on a patient or portions of a patient's clothing. Appliqué 29 and/or another member 29' may have any type of shape or image thereon for use with the intended patient.

Elongated strip wrap member 10' may be used to allow the pulse oximetry sensor 1 (see, FIG. 13) of the present invention to be applied to larger patients in the range from neonates to adults.

The individual tapes of each type of disposable wrap member 10 and 10' discussed herein are formed as being connected in an end-to-end relationship having a perforation 13 or 13' located between each adjacent wrap member 10 or 10'. For convenience, wrap members 10 and 10' are packaged in a dispenser box, such as 100 wrap members 10, 10' wound as a roll, typically without the use of a winding spool. However, the present invention contemplates using a winding spool, such as a two (2) inch internal diameter spool, if desired. At least one or more rolls of wrap members are typically included in each package. This type of compact packaging allows the wrap members of the present invention to be conveniently placed in storage, for instance, stored on a shelf in a patient's room. Additionally, because many types of patients exhibit positive effects from receiving appliqués 29, particularly patients in pediatric dentist offices and doctors offices, an attached appliqué 29 to the pediatric version of the wrap members is present, i.e., the smaller versions of butterfly wrap member 10 and the elongated wrap member 10'. Providing an appliqué 29 serves to emotionally benefit the pediatric patient and thereby allows for easier application of a pulse oximetry sensor by the clinician.

Figure 5:
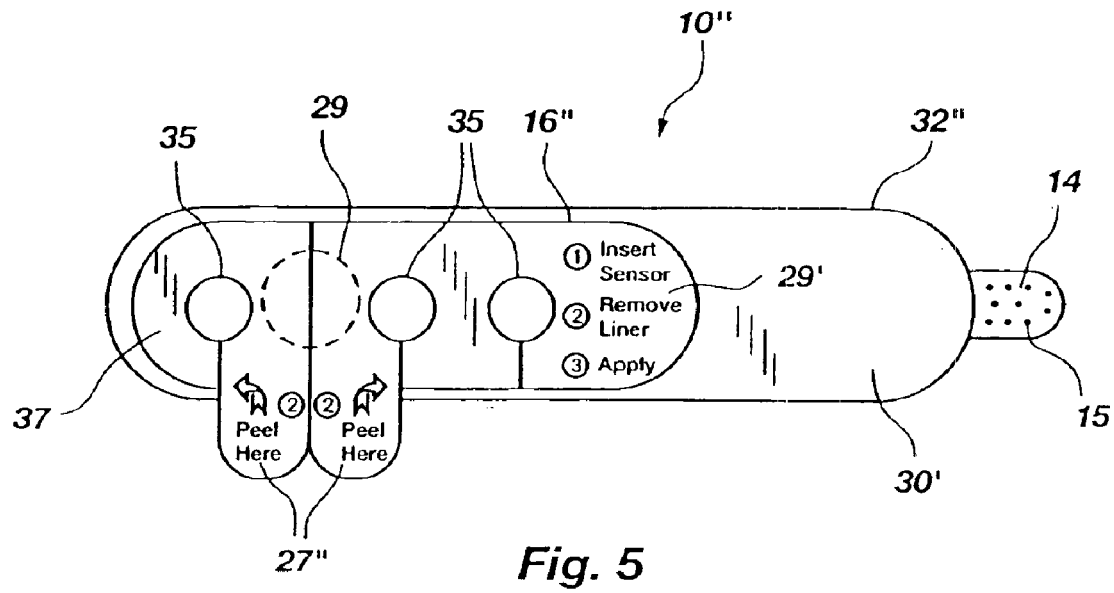
FIG. 5 is a rear view of a yet another embodiment of the disposable wrap member of the present invention.
Figure 6:
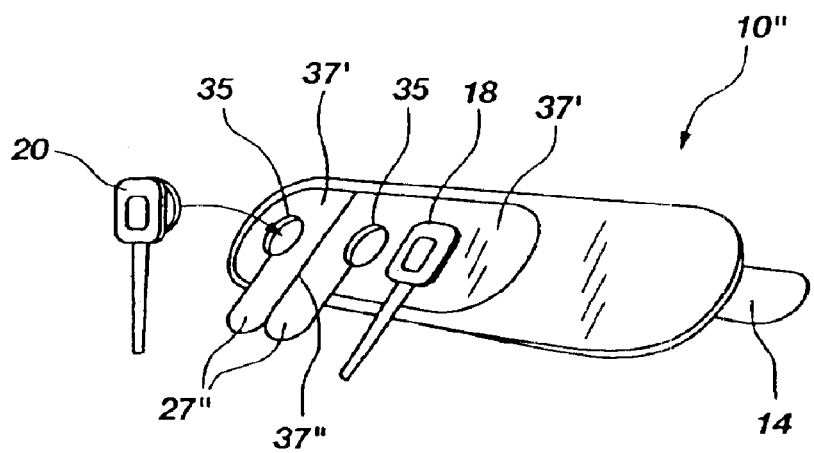
FIG. 6 is a perspective view of the rear of the embodiment of the disposable wrap member of the present invention depicted in FIG. 5 having an LED assembly and photodiode for insertion therein.
Figure 7:
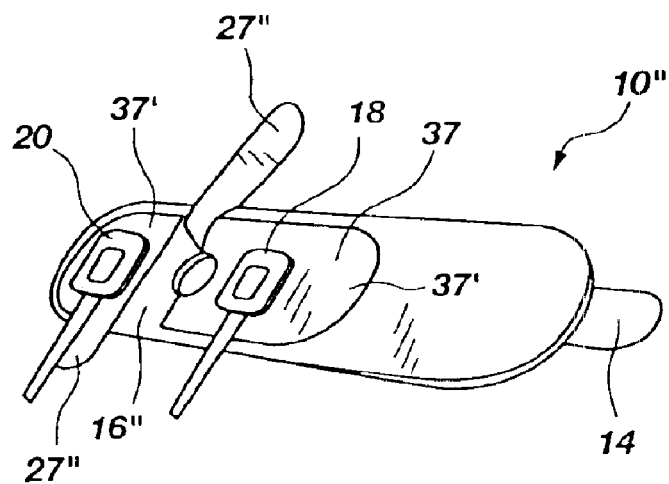
FIG. 7 is a perspective view of the rear of the embodiment of the disposable wrap member of the present invention depicted in FIG. 5 having an LED assembly and photodiode insert therein and a portion of the release liner being removed therefrom.

Referring now to FIGS. 5–7, another embodiment of the present invention is illustrated from the rear thereof. Wrap member 10" comprises foam lamination having a fabric cover 32" thereover and a fastener 14 attached thereto, as well as a plurality of apertures 35 formed therein to retain portions of the LED assembly 18 and photodiode 20 therein. A foam portion 30' of wrap member 10" comprises any suitable type foam, such as a polyester foam, or any suitable compliant substrate, foam substrate, comfortable foam substrate, or plastic foam substrate as the foam member. Fabric portion 32" of wrap member 10" comprises any suitable fabric, such as a fabric having a plurality of loops integrally formed therein, which may be readily engaged by a plurality of fastening members located on fastener 14 of wrap member 10".

Fastener 14 attached to wrap member 10" comprises a molded plastic member having a plurality of hooks 15 formed on one surface thereof to engage the plurality of loops (not shown) formed in fabric portion 32" of wrap member 10". The combination of fastener 14 having a plurality of hooks 15 formed on one surface thereof and fabric portion 32" of wrap member 10" is commonly referred to as a VELCRO® type fastener comprised of synthetic materials which adhere when pressed together. Foam portion 30' and fabric portion 32" of wrap member 10" are secured together by any suitable means of fastening, such as adhesive bonding. Fastener 14 of wrap member 10" is secured to foam portion 30' and fabric portion 32" of wrap member 10" by any suitable means, such as adhesive bonding, sewing, ultrasonic staking, or the natural tendencies of the materials to adhere to one another.

An adhesive member 16" located on wrap member 10" may be any suitable type, such as a double-sided adhesive tape coated with a suitable adhesive, one side of adhesive member 16" being adhesively secured to wrap member 10", while the other side thereof initially has a paper, or other suitable material, covering 37, i.e., a release liner, releasably retained thereover which is removed for installation of the oximetry sensor 1 (see, FIG. 13) of the present invention on a patient.

Release liner 37 includes portions thereof 37', each having a tab 27" to allow ready removal of portions 37' from the adhesive therebelow. As shown, adhesive member 16" is a generally rectangular shaped member secured to wrap member 10". If desired, adhesive member 16" may be of any other suitable shapes, such as an annular member. Adhesive member 16" is used to retain the oximetry sensor 1 (see, FIG. 13) of the present invention in position on a patient while the fastener 14 retains the sensor 1 on the patient.

Alternately, rather than using a double-sided adhesive member 16", adhesive member 16" may be a soft, compliant elastomeric member, such as a silicone elastomeric member, having an adhesive coating on one side thereof to retain adhesive member 16" on wrap member 10" with the friction of the soft elastomeric member against the skin of a patient being sufficient to retain wrap member 10" in position without requiring the wrap member to be tightly wrapped about the patient's finger or the like causing discomfort.

Referring to FIG. 6, in particular, release liner 37 features a two-part wrap-around design including release liner portions 37' that allows an LED assembly 18 and photodiode 20 therein to be assembled with elongated strip wrap member 10" prior to the removal of release liner 37. This feature facilitates the assembly process and sharply reduces the chances that a member of a clinical staff will get stuck or tangled with the adhesive located on adhesive member 16" on which release member 37 is removably retained during assembly of the LED assembly 18 and photodiode 20 therein to wrap member 10". Release liner 37 consists of two parts 37' having release tabs 27" for use by members of a clinical staff or any other user to pull or release release liner 37 from the foam and fabric underlying substrate prior to applying the wrap member to the patient. Additionally, a slit 37" is provided in release liner 37 that allow each part 37' of release liner 37 to be peeled around the assembled LED assembly 18 and photodiode 20 therein separately and independently of the other part.

Additionally, release liner 37 may contain an appliqué 29 (shown in dotted line in FIG. 5) adhesively attached to a portion of release liner 37 and may contain another member 29', for example, having instructions thereon, which may be adhesively attached to a portion of release liner 37 or printed thereon. Any suitable adhesive may be used to attach the appliqué 29 to release liner 37, which is also suitable for use with the appliqué 29 on a patient or portions of a patient's clothing. Appliqué 29 may have any type of shape or image thereon for use with the intended patient.

Referring now to FIG. 7 in particular, a portion 37' of release liner 37 is illustrated as being peeled away from adhesive member 16" on wrap member 10" after the LED assembly 18 and photodiode 20 have been installed in the wrap member. Tab 27" is used to separate a portion 37' of release liner 37 from the adhesive to be removed from around either LED assembly 18 or photodiode 20.

Figure 8:
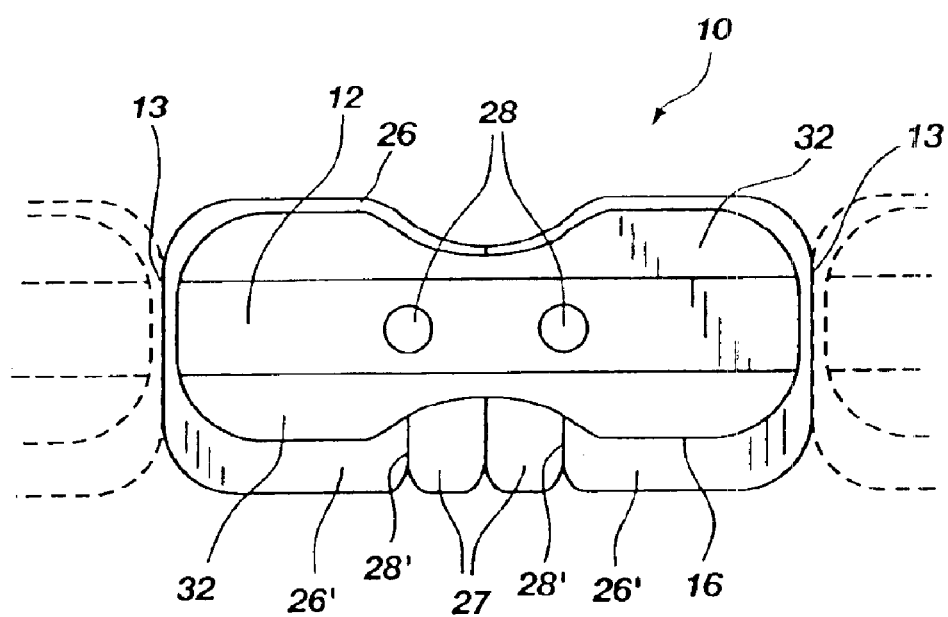
FIG. 8 is an enlarged front view of the embodiment of the disposable butterfly wrap member of the present invention depicted in FIGS. 1 and 2A.

Referring to FIG. 8, an enlarged view of at least one butterfly wrap member 10 illustrated in drawing FIGS. 1, 2A and 2B is illustrated. As previously stated, butterfly wrap member 10 comprises fabric covering 32, which may include a foam lamination portion having a fabric cover, and a plurality of apertures 28 for portions of an LED assembly 18 (not shown) and photodiode 20 (not shown) therein. The foam portion of wrap member 10 may be included as part of butterfly wrap member 10 comprising any suitable type foam, such as a polyester foam, or any suitable compliant substrate, foam substrate, comfortable foam substrate, or plastic foam substrate as the foam member. Fabric portion 32 of butterfly wrap member 10 comprises any suitable fabric, which may be readily engaged by the adhesive on the other side of the wrap member 10. The foam portion, if used, and fabric portion 32 of wrap member 10 are secured together by any suitable means of fastening, such as adhesive bonding.

Located on the other side of butterfly wrap member 10 is an adhesive member 16 over or covering at least portions of optional foam portion 30 of wrap member 10. Adhesive member 16 located on the wrap member 10 may be any suitable type, such as a double-sided adhesive tape coated with a suitable adhesive, one side of adhesive member 16 being adhesively secured to wrap member 10, while the other side thereof initially has a paper, or other suitable material covering, e.g., a release liner 26, releasably retained thereover which is removed for installation of the oximetry sensor 10 of the present invention on a patient. Adhesive member 16 may have the shape of butterfly wrap member 10 to completely cover one side thereof or may be any convenient shape, such as a generally rectangular shaped member secured to wrap member 10. If desired, adhesive member 16 may be of any other suitable shapes, such as an annular member.

Adhesive member 16 is used to retain the oximetry sensor of the present invention in position on a patient. As illustrated, an individual butterfly wrap member 10 includes a cover strip 12 over a portion of one side, e.g., the front side of butterfly wrap member 10, and apertures 28 for an LED assembly 18 (not shown) and photodiode 20 (not shown). As further illustrated, portions of a release liner 26 attached to portions of the opposing side, e.g., the back side (not shown) of the butterfly wrap member 10.

Figure 9:
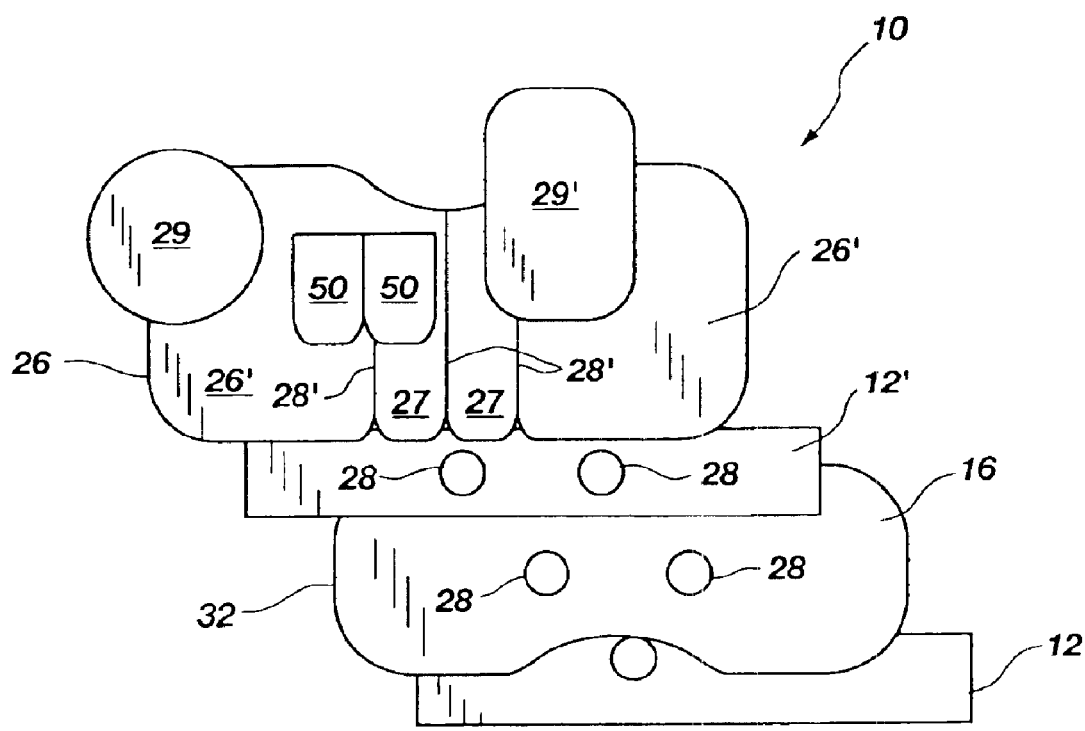
FIG. 9 is an enlarged exploded rear view of the embodiment of the disposable butterfly wrap member of the present invention depicted in FIGS. 1 and 2B.

Referring to FIG. 9, the present invention contemplates that butterfly wrap member 10 includes, on the opposing or back side, a center strip 12', such as the cover strip 12, attached to wrap member 10 by means of adhesive 16 on foam/fabric portion of butterfly wrap member 10, a release liner 26 featuring a two-part wrap-around design including release liner portions 26' that each allows an LED assembly 18 (not shown) and photodiode 20 (not shown) to be assembled with butterfly wrap member 10 prior to the removal of the release liner 26. Again, this feature of the present invention facilitates the assembly process and sharply reduces the chances that a member of a clinical staff or other use will get stuck or tangled with the adhesive of adhesive member 16 having release liner 26 removably retained thereon during assembly of the LED assembly 18 (not shown) and photodiode 20 (not shown) therein to butterfly wrap member 10. Release liner 26 consists of two parts 26' each having a release tab 27 for use by members of a clinical staff or other user to pull or release release liner 26 from foam/fabric portion 32 prior to applying the wrap member to the patient. In the embodiment of FIG. 9, each tab 27 contains a label 50 thereon to identify tab 27 to a user.

Additionally, slits 28' are provided in release liner 26 to allow each part 26' of the release liner to be peeled around the assembled LED assembly 18 (not shown) and photodiode 20 (not shown), each being located in an aperture 28 in butterfly wrap member 10. Additionally, as illustrated, release liner 26 contains an appliqué 29 adhesively attached to a portion of the release liner and another member 29', for example, having instructions thereon, which may be adhesively attached to a portion of release liner 26 or printed thereon. Any suitable adhesive may be used to attach the appliqué 29 to release liner 26, which is also suitable for use with applying appliqué 29 on a patient or portions of a patient's clothing. Appliqué 29 may have any type of shape or image thereon suitable for use with the intended patient.

Figure 10:
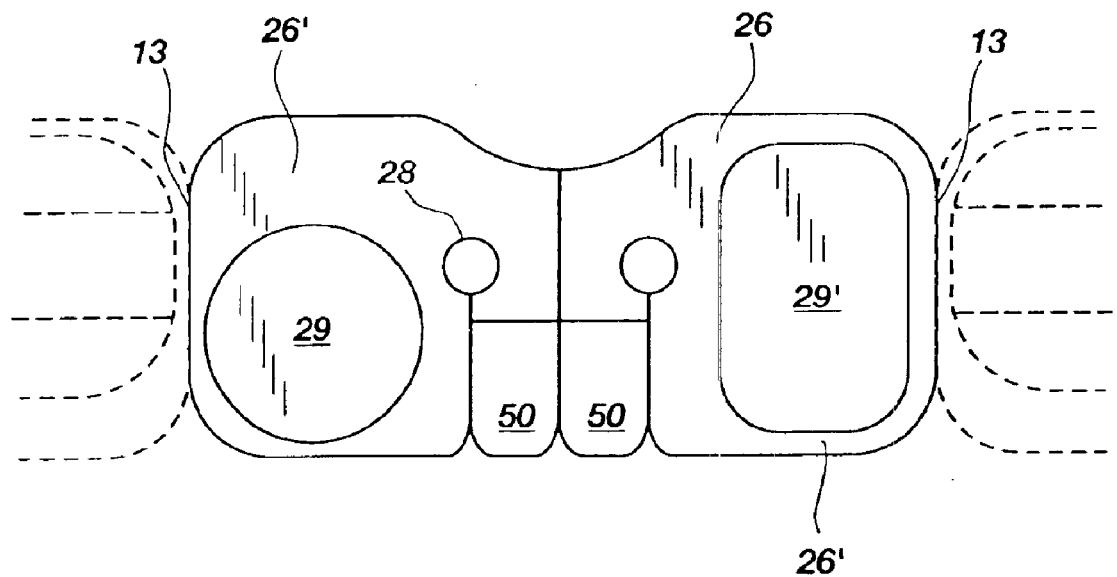
FIG. 10 is an enlarged rear view of the embodiment of the disposable butterfly wrap member of the present invention depicted in FIGS. 1 and 2B.

Referring to FIG. 10, butterfly wrap member 10 is illustrated in an enlarged view showing the perforations 13 between adjacent wrap members 10 when in strip form and the locations of the appliqué 29, instructions 29' and additional instructions or information 50 on tabs 27 of release liner 26.

Referring to FIG. 11, photodiode 20 includes a housing 125 in the shape of a geometric rectangular solid, one face of which is framed by an integral rectangular flange 129. Similarly, LED assembly 18 includes a housing 127, which is in the shape of a geometric rectangular solid, one face of which is framed by an integral rectangular flange 131. Housings 125 and 127 are interconnected by a connecting member 126 and preferably formed from a soft pliant rubber-like material and include projections 133 and 135 therefrom which include flanges 137 and 139, respectively, that are received in apertures 28 of adhesive wrap member 10, 10', 10" to releasably retain the photodiode 20 and LED assembly 18 therein. Flanges 137 and 139 may be of any suitable shape, such as rectangular, circular, elliptical, or ovoid. Similarly, housings 125 and 127 may be of any suitable shape, such as rectangular or circular. Flanges 129 and 131 of housings 125 and 127, respectively, include a covering 140 and 142, respectively, thereover having a window portion therein to allow infrared light from LED assembly 18 to be visible and transmitted therethrough to be detected by photodiode 20. A cable 22 includes wires 24 connected to photodiode 20 and LED assembly 18.

Referring to FIG. 12, an electrical assembly 36 of the oximetry sensor 1 (see, FIG. 13) of the present invention is illustrated. A cable 22 is provided with a suitable connector 40 on one end thereof while LED assembly 18 and photodiode 20 are installed on appropriate wires 24 of cable 22 on the other end thereto. Cable 22, connector 40, wires 24, LED assembly 18, and photodiode 20 are reusable and capable of being sterilized using suitable known sterilization procedures commonly available.

Referring to FIG. 13, wrap member 10" has adhesive member 16" installed thereon the foam portion (not shown) of the wrap member as an adhesive coating on each side thereof. Adhesive member 16" contains a release liner 37 thereon to be removed prior to the installation of the wrap member on a patient. As shown, adhesive member 16 is a rectangular shaped member which surrounds the apertures 35 in the wrap member used to mount the LED assembly and the photodiode.

Still referring to FIG. 13, the completed subassembly 36 is shown including cable 22 having a connector 40 on one end thereof and LED assembly 18 and photodiode 20 on the other end thereof. The completed subassembly 38 of wrap member 10" having adhesive member 16" having, in turn, release liner 37 thereon being adhesively retained on the wrap member. Subassembly 36 is joined to the subassembly 38 by flanges 137 and 139 of photodiode 20 and LED assembly 18, respectively, being inserted into apertures 28 of the wrap member. In this manner, subassembly 36 is securely mounted in the desired position thereon by flanges 137 and 139 engaging one side of the wrap member while flanges 129 and 131 of photodiode 18 and LED assembly 20, respectively, engage the opposing side thereof.

Figure 14:
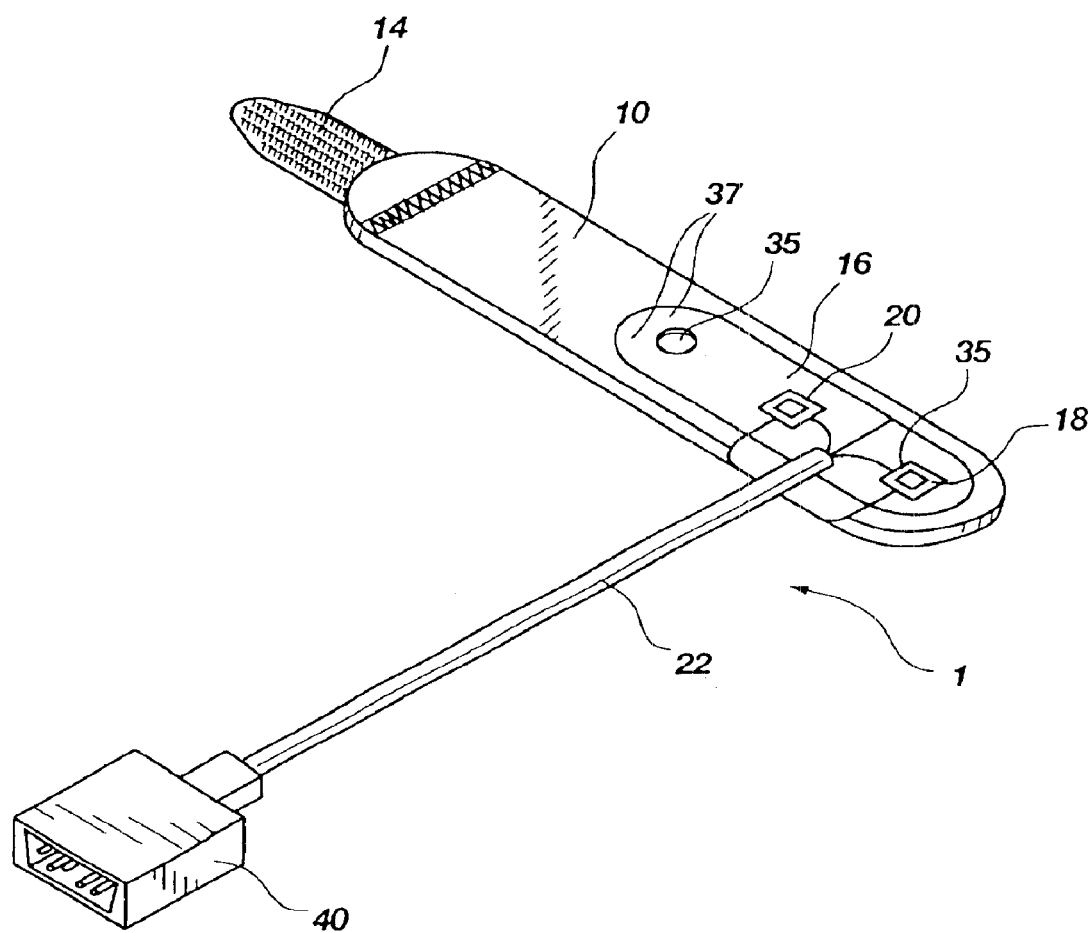
FIG. 14 is a view of a pulse oximetry sensor of the present invention having a disposable wrap member, LED assembly, photodiode, cable, and connector.

Referring to FIG. 14, the oximetry sensor 1 of the present invention is shown in its assembled, completed form readily for use on a patient. Oximetry sensor 1 including a wrap member 10" including a fastener 14, adhesive member 16" initially having a release liner 37 thereover, LED assembly 18, and photodiode 20 connected to a cable 22 having connector 40 thereon.

Figure 15:
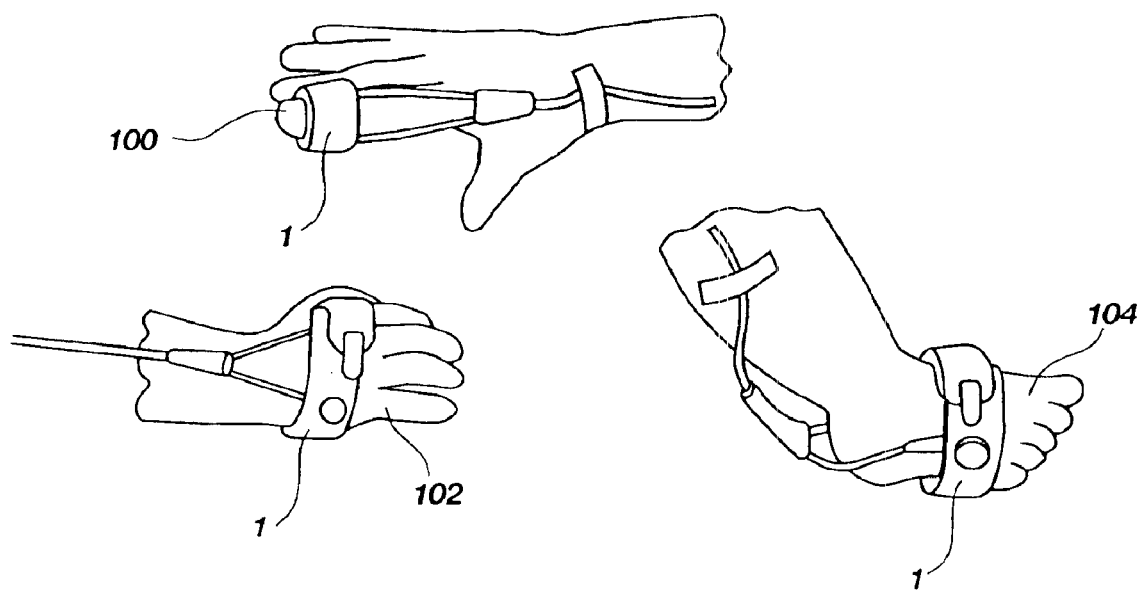
FIG. 15 is a view of the embodiment of the disposable wrap member of the present invention depicted in FIG. 5 having an LED assembly mounted on a pediatric finger, neonatal/infant hand and neonatal/infant foot, respectively, of a user.

Referring to FIG. 15, oximetry sensor 1 of the present invention is shown having either an elongated strip wrap member 10 or wrap member 10' or 10" as described herein alternately located on the finger 100, hand 102, or foot 104 of a neonatal patient.

From the foregoing it is easily seen that the oximetry sensor 1 of the present invention offers many advantages over the prior art sensors. The oximetry sensor 1 is generally easily manufactured from inexpensive materials, is easy to use on a patient, is easy to reuse on a patient, and is comfortable in use on a patient. Because the oximetry sensor of the present invention uses an adhesive member 16, 16', 16" to attach the sensor to a patient, the sensor is quickly applied to a patient having adhesive contacting the skin of a patient to retain the sensor in position without causing discomfort from the wrap member 10, 10', 10" being too tightly secured to the patient. The oximetry sensor of the present invention is easily adjustable and has an extended life in comparison to solely adhesively retained sensors. Oximetry sensor 1 also is easy to reposition on a patient for optimum signal and comfort.

Additionally, because wrap member 10, 10', 10" is conformable and compressible, the oximetry sensor may be easily repositioned on a patient without unwrapping the sensor from the patient while the adhesive member 16 retains the sensor in the desired position. The combination of the foam wrap and fabric back as in wrap member 10" provides comfort to the patient and a readily conformable sensor. The foam wrap and fabric back also allows the sensor to breathe and help minimize sweating of a patient. Because the oximetry sensor of the present invention is not solely retained on the patient through the use of adhesives, the sensor is very suited to patients who may be sensitive or have allergies to adhesives. As previously stated, the sensor is nontraumatic during use since it is conformable and compressible. Because the oximetry sensor is simple to manufacture from relatively inexpensive materials, it is disposable but has a long life during use as compared to adhesive type sensors as well as being readily reusable on a patient. The oximetry sensor 1 of the present invention may be readily trimmed to customize the application of the sensor to a patient. Additionally, the electrical assembly of oximetry sensor 1 may be sterilized if so desired since the materials from which the sensor is made will accept sterilization.

Additionally, because wrap member 10, 10',10" of the present invention may be provided in roll form for storage and ready access, a different wrap member 10, 10', 10" may be provided for use on the same patient or the use of the pulse oximetry sensor 1 on a different patient in the same room or same area since a supply of the wrap members 10 is readily available for use. In this manner, it is not required to keep assembled pulse oximetry sensors 1 available at all times in the same area.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An oximetry sensor comprising:
a body member having a plurality of apertures therein;
an adhesive disposed on the body member surrounding the plurality of apertures;
a release liner configured for removal from the adhesive, wherein the release liner includes a first portion disposed around a first aperture in the plurality of apertures and a second portion disposed around a second aperture in the plurality of apertures, wherein the first portion and the second portion are separately removable from the body member such that the adhesive disposed in a perimeter around the first and the second apertures are separately exposed, and wherein the first and the second portions each include a release tab to facilitate removal of the first and the second portions from the body member;
an LED assembly secured in the first aperture; and
a photodiode secured in the second aperture.

2. The oximetry sensor of claim 1, wherein the body member comprises a compliant portion and a cloth fabric portion.

3. The oximetry sensor of claim 1, further comprising a fastener coupled to the body member for securing the wrap member to a patient, wherein the fastener is a hook and loop fastening system.

4. The oximetry sensor of claim 1, wherein the adhesive is adhesively secured to the body member, and wherein the adhesive includes an appliqué removably coupled therewith, another member coupled therewith, or any combination thereof.

5. The oximetry sensor of claim 1, wherein the release liner includes an appliqué adhesively coupled therewith, another member adhesively coupled therewith, or any combination thereof.

6. The oximetry sensor of claim 1, further comprising at least one cover located on at least a portion of each side of the body member.

7. A disposable wrap member comprising:
a body member having a plurality of apertures therein;
an adhesive disposed on the body member; and
a release liner overlying the adhesive, wherein the release liner is configured for removal from the adhesive, wherein the release liner includes a first portion disposed around a first aperture in the plurality of apertures and a second portion disposed around a second aperture in the plurality of apertures, wherein the first portion and the second portion are separately removable from the body member such that the adhesive disposed in a perimeter around the first and the second apertures are separately exposed, and wherein the first and the second portions each include a release tab to facilitate removal of the first and the second portions from the body member.

8. The wrap member of claim 7, further comprising an appliqué removably coupled to the adhesive or to the release liner.

9. The wrap member of claim 7, wherein the body member comprises a foam substrate.

10. The wrap member of claim 7, wherein the body member comprises a compliant substrate covered by a cloth member.

11. The wrap member of claim 7, further comprising another body member connected to the body member, and wherein perforations are provided between the body member and the another body member.

12. The wrap member of claim 7, wherein the body member is provided as a roll of body members, each body member connected to an adjacent body member and having perforations located therebetween.

13. The wrap member of claim 7, wherein the body member comprises a foam portion and a fabric portion.

14. The wrap member of claim 7, further comprising a fastener coupled to the body member, wherein the fastener is a hook and loop fastener.

15. The wrap member of claim 7, wherein the body member has a butterfly shape or an elongated strip shape.

* * * * *